United States Patent [19]

Suskind et al.

[11] Patent Number: 4,929,498

[45] Date of Patent: May 29, 1990

[54] ENGINEERED-PULP WET WIPER FABRIC

[75] Inventors: Stuart P. Suskind, Greer; Joseph H. Miller, Greenville, both of S.C.

[73] Assignee: James River Corporation of Virginia, Norwalk, Conn.

[21] Appl. No.: 304,981

[22] Filed: Jan. 31, 1989

[51] Int. Cl.$^5$ .................. A01N 25/34; A61F 13/15; A61L 15/46; D21H 11/16; D21H 21/36

[52] U.S. Cl. .................. 428/288; 156/62.4; 162/135; 162/141; 162/161; 162/163; 206/812; 428/296; 428/297; 428/299; 428/301; 428/306.6; 428/308.8; 428/447; 428/452; 604/360; 604/374; 604/378; 604/383

[58] Field of Search .................. 162/141, 161, 163; 424/404, 411; 428/288, 296, 297, 299, 300, 301, 306.6, 308.8; 604/360, 374, 378, 383

[56] References Cited

U.S. PATENT DOCUMENTS 2,474,306 6/1949 Doub .
3,264,172 8/1966 Regutti .
3,728,213 4/1973 Hinz .
3,860,709 1/1975 Abbott et al. .
4,259,103 3/1981 Malek et al. .
4,408,996 10/1983 Baldwin .
4,615,937 10/1986 Bouchette .

OTHER PUBLICATIONS

Hayes et al, "How Antimicrobial Treatment Can Improve Nonwovens", *American Dyestuff Reporter*, Jun. 1984, pp. 35-40 and 44-45.

*Primary Examiner*—James C. Cannon
*Attorney, Agent, or Firm*—Richard J. Gallagher

[57] ABSTRACT

Discolsed are wet wiper products that incorporate antimicrobially-active nonwoven fabrics, preferably comprising: bonded fibers; a binder distributed on said fibers; and an antimicrobial agent distributed on from 10% through 50% of said fibers, said antimicrobial agent being substantive to said fibers such that said antimicrobial agent is prevented from substantially diffusing from said fabric.

18 Claims, No Drawings

ENGINEERED-PULP WET WIPER FABRIC

BACKGROUND OF THE INVENTION

1. Field of the Invention

The present invention relates to nonwoven fabric webs. More particularly, this invention relates to antimicrobially-active nonwoven webs, to methods for making such webs, and to wet wipers containing such webs.

Wet wiper products should have antimicrobial properties in order to destroy or inhibit the growth of various microorganisms, including bacteria, yeasts, and molds, whose growth is promoted by the moist conditions prevailing in said products. There are at least four approaches that have been used to obtain some type of antimicrobial protection in wet wiper products: substrate pore size control; sterilization; chemical surface treatment; and chemical saturation.

2. Description of the Prior Art

The primary method of antimicrobial control and protection currently used in wet wiper products is that which is achieved by a chemical permeation of preservative agents throughout the wet wiper product. This permeation may be achieved by padding the wiper fabric during its manufacture and/or by incorporating the chemicals in the liquid or lotion phase of the wiper product. Padding the fabric is generally not favored as a commercial technique, however, because of the additional manufacturing processing costs associated therewith. Since a liquid or lotion must be applied to the fabric in a wet wiper product in any event, and since the liquid or lotion without antimicrobial control or preservation agents would present a prime opportunity for microbiological growth, a preferred method of applying the chemical preservation or antimicrobial control has been to incorporate soluble preservative agents in the lotion phase and then associate the preserved lotion with the fabric. In both of these permeation scenarios, the end result is the same. Since the preservatives and antimicrobial agents are soluble in the liquid or lotion phase, they ultimately equilibrate through the wet wiper product and provide a homogeneous chemical method of antimicrobial control. When a wet wiper product of this type is used by the consumer, the antimicrobial agents from the liquid or lotion phase remain behind on the user's skin. Many individuals exhibit adverse reactions to such preservatives. Hence consumer use of the wet wiper product is significantly impeded. Both insolubility and antimicrobial-spectrum-activity considerations significantly limit the use of hypoallergenic preservatives in the liquid wetting solution.

U.S. Pat. No. 4,615,937 teaches a means for incorporating the antimicrobial properties required in the wet wiper product in a manner substantive to and within the wet wiper fabric. The issues of solubility and antimicrobial-activity-spectrum are overcome because no harmful residue is left on the skin of the user. In addition, the increased costs of padding the wet wiper fabric during its manufacturing process can be avoided by incorporating these substantive antimicrobials into the synthetic bonding agent typically already required for such nonwoven fabrics.

In the wet wipe system described in U.S. Pat. No. 4,615,937, however, the antimicrobial agent renders the substrate hydrophobic and needed absorbency properties are lost. To remedy this, a wetting agent can be incorporated into the fabric. Wetting agents, however, may restore only a portion of the original absorbency qualities of the fabric. Furthermore, while appropriate wetting agents are suitable for most applications, it would be desirable for some uses—for example in burn and wound management—to simplify the chemical additive system employed by eliminating these compounds.

SUMMARY OF THE INVENTION

We have now developed an antimicrobially-active nonwoven fabric web that overcomes the inherent and significant disadvantages present in previous nonwoven webs that exhibit antimicrobial properties. Through an appropriate pretreatment of some but not all of the pulp fibers that make up the web, the necessity for the use of wetting agents is eliminated. According to the present invention, nonwoven fabrics—such as airlaid, wetlaid, and hydroentangled—are envisioned whereby a portion (for example, from about 10-50%) of the normal pulp charge is replaced by the antibacterially-modified pulp. Fabrics formed in this way show both adequate bioactivity and good absorbency without the necessity for chemical wetting agents.

In the prior art manufacture of bioactive fabrics by incorporation of antimicrobial into the binder, process and product control are limited by compatibility of chemicals in the bath, by pick-up and cure rate due to line speed, by low chemical efficiency due to encapsulation by the binder, and so on. In the present invention, such limitations are avoided. The antimicrobial pulp prepared in a separate step is controlled with respect to purity, level of treatment, and degree of chemical bonding between the antimicrobial and the pulp.

While in the preferred embodiments of the present invention a binder is used, in an alternative embodiment, the use of binder can be avoided altogether. A wet wiper web requiring no binder, such as a hydroentangled web, can be prepared from the engineered pulp of the present invention.

Based upon these benefits, the present invention represents a significant advance in the state of the art. The foregoing and other features and advantages of the present invention will be made more readily apparent by the following description of the preferred embodiments.

DESCRIPTION OF THE PREFERRED EMBODIMENTS

The method provided by the present invention produces a nonwoven fabric web that is antimicrobially active. The fabric according to the invention in its broadest aspect is an antimicrobially-active nonwoven fabric suitable for use as a wet wiper that comprises fibers and an antimicrobial agent distributed on from 10% through 50% of said fibers, said antimicrobial agent being substantive to said fibers such that said antimicrobial agent is substantially prevented from diffusing from said fabric.

Initially, a preferred method according to the present invention forms an unbonded fibrous web from a pulp mixture that contains a minor portion of pulp that has been treated with an antimicrobial agent and a major portion of pulp that has not been so treated. An uncured binder is then applied to the unbonded fibrous web, with the antimicrobial agent being substantive to the fibers of the web when the web is either bonded or unbonded and when the web is wet as well as when the web is dry. After application of the binder, the binder is cured to bind the fibers together to form an antimicrobially-active nonwoven web.

The Pulp

Although various cellulosic and synthetic fibers known in the art can be effectively used, the pulped fibers from which the webs according to the present invention are produced are preferably cellulosic fibers and, more preferably, wood pulp fibers. A portion of the cellulosic fibers, such as wood pulp fibers, are treated with antimicrobial and if desired are predried prior to forming. Examples of wood pulp fibers include various mechanical and chemical pulp fibers, such as cedar fibers, Southern pine fibers, spruce fibers, and hemlock fibers. The particular cellulosic fibers selected to make the nonwoven web depend, in part, upon the type of texture, such as soft, woolly, or fluffy, and the porosity of the web that is desired. Alternatively, the fibers can be a combination of cellulosic and synthetic fibers.

Antimicrobial treatment of a portion of the pulp may be accomplished as follows: a pulp slurry in water containing dissolved organosilicon quaternary ammonium compound is allowed to absorb a predetermined quantity of the agent. The pulp is then filtered and heated to remove water and react the agent with the surface hydroxyl groups of the cellulose. The modified pulp is then washed to remove unreacted organosilicon and finally dried.

The weight of the fibers used to form the unbonded fibrous web can vary depending upon the ultimate nonwoven web that is produced. Typically, the weight of the fibers forming the web will vary within the range of about 5 pounds per ream to about 60 pounds per ream. From 10% through 50%, preferably from 15% through 25%, of the fibers used to make the web will be those that have been pre-treated with antimicrobial.

Various web-forming techniques known in the art can be effectively used to form the unbonded fibers. The web can be formed by standard nonwoven technologies, such as by airlaying the web or by wetlaying the web. Treated pulp fibers can also be combined with other nonwoven fabrics—such as meltblown, spunbonded, needle punched, and hydroentangled—to also provide binderless antimicrobially-active webs.

The Antimicrobial Agent

The antimicrobial agent is selected to be substantive to the web when the web is wet as well as when it is dry. An antimicrobial agent is considered to be substantive to the web if the antimicrobial agent attaches directly to the fibers of the web without the need for an additional adhesive substance. Substantive antimicrobial agents do not substantially diffuse from the fibers or the binder used to bind the fibers together if any. U.S. Pat. Nos. 3,860,709 and 4,259,103 and Hayes et al., "How Antimicrobial Treatment Can Improve Nonwovens", *American Dyestuff Reporter*, pages 35-40 and 44-45, discuss generally the nonleachability of various antimicrobial agents from substrates. Preferred antimicrobial agents are organosilicon quaternary ammonium salts, such as silyl-quaternary ammonium salts. Preferred organo-silicon quaternary ammonium salts are those having the formula

in which R is lower alkyl, n is an integer from 2 through 8, $R_1$ is an alkyl group of 9 through 22 carbon atoms, $R_2$ and $R_3$ are lower alkyl, and X is a pharmaceutically acceptable anion. Specific embodiments thereof include 3-(trimethyoxysilyl)propyldodecyldimethylammonium salts, such as 3-(trimethoxysilyl)propyldodecyldimethylammonium chloride, and 3-(trimethoxysilyl)-propyloctadecyldimethylammonium salts, such as 3-(trimethoxysilyl)propyloctadecyldimethylammonium chloride.

The antimicrobial agent is preferably applied to the pulp portion to be treated prior to application of the binder. Although various amounts of the antimicrobial agent may be applied to the web depending upon, in part, the fibers selected and the particular binder used, the amount of the antimicrobial active agent is typically in the range of about 0.25% to about 3% of the total final web weight.

The antimicrobial agent is selected to be substantive to the binder where one is used in addition to being substantive to the fibers of the web. Hence, such an antimicrobial agent attaches directly to the binder and to the cellulosic fibers without the need for an adhesive substance. Likewise, the ionic character of the binder is carefully chosen so that the antimicrobial active agent is usually substantially inert with respect to the binder polymer and emulsion system to prevent ionic interaction of the antimicrobial agent and the binder.

Many of the antimicrobial agents useful in the present invention are commercially available. Others can be prepared by various techniques known in the art. For example U.S. Pat. Nos. 4,406,892, 4,282,366, 4,394,378, and 4,408,996 describe various organosilicon quaternary ammonium compounds, especially silyl quaternary ammonium compounds, and methods for preparing such compounds. Likewise, articles in the scientific literature, such as Walters et al., "Algicidal Activity of a Surface-Bonded Organosilicon Quaternary Ammonium Chloride", 25 *Applied Microbiology*, 253–256 (1972) and Isquith et al., "Surface-Bonded Antimicrobial Activity of an Organosilicon Quaternary Ammonium Chloride", 24 *Applied Microbiology*, 859–863 (1972). also disclose methods of making various organosilicon quaternary ammonium compounds. Thus, the skilled artisan can readily select a method for preparing the desired organosilicon quaternary ammonium compound to be used in the practice of the present invention.

Other antimicrobial agents that are substantive to the fibers and the binder may also be used. In the case of wet wipers, the governing criteria are substantivity, antimicrobial activity, and safety, such that the wet wiper is safe for use on human skin and eyes.

The Binder

In accordance with the currently preferred aspect of the present invention, an uncured binder is applied throughout the unbonded fibrous web, with the antimicrobial agent being substantive to the fibers of the web and to the binder when the web is either bonded or unbonded and when the web is wet as well as when it is dry. Various binders known in the art can be used. A preferred binder is a polymeric binder such as a latex binder. Acceptable latex binders include acrylate emulsions, butadiene-styrene emulsions, acrylonitrile-butadiene emulsions, and ethylene/vinyl acetate emulsions. One effective latex binder is the ethylene/vinyl acetate which is sold under the trademark AIRFLEX A-410 by Air Products. The binder system used can also include a mixture of anionic and nonionic binders, such as ethylene/vinyl acetate which is sold under the trademark AIRFLEX A-106 by Air Products, and the ethylene acetate which is sold under the trademark HA-8 by Rohm & Haas.

The amount of the binder that is to be applied to the fibers depends, in part, upon the type of fibers, such as cellulosic, and the antimicrobial agent being used in the nonwoven web. Typically, the amount of the binder applied to the fibers varies within the range of about 5% to about 30%. Similarly, the amount of solids in the binder, especially a latex binder, depends among other things upon the weight of the fibers in the nonwoven web. Generally, latex binders have from about 5% to about 25% solids are used. Of course, the skilled artisan can select the particular binder, the amount of the binder used, and the amount of solids present in the binder depending upon, in part, the type of fibers that are to be bound.

Various application methods and apparatuses known in the art can be readily selected by the skilled artisan for applying the binder to the web. The binder is applied to the fibers by various techniques well known in the art, such as spraying, foaming, in a bath, or even by padding or printing. For example, the uncured binder may be sprayed onto unbound fibers, such as celluosic fibers, that have been airlaid on a foraminous support. Sililarly, the uncured binder can be contained in a bath through which the unbonded biers pass.

In accordance with the present invention, the binder material is cured to bind the fibers together to form an antimicrobial nonwoven web. Various curing techniques known in the art, such as infrared radiation, electron beam radiation, and forced hot air, can be effectively selected and used by the skilled artisan to achieve the proper degree of binder cure.

Wet Wipers

The present invention provides an antimicrobially-active nonwoven fabric web. The nonwoven web has bonded fibers; a binder substantially uniformly distributed on the fibers, the binder being present in an amount effective to bind the fibers; and an antimicrobial agent substantially uniformly distributed on a portion of the fibers, the antimicrobial agent being substantive to the fibers when the web is either wet or dry. The amount of the antimicrobial agent present within the nonwoven web is preferably in the range of about 0.1% to about 3% of the total web weight. The amount of the binder present within the nonwoven web is preferably in the range of about 5% to about 30% of the total web weight. When the antimicrobially-active nonwoven web of the present invention is present in a substantially preservative-free liquid, a uniquely attractive antimicrobially-active wet wiper is achieved. The substantially preservative-free liquid, such as water, maintains the web in a wet condition until use.

EXAMPLES

The following examples are illustrative of the present invention.

Example 1

Two thousand pounds of wood pulp are charged into a hydropulper along with 12,000 gallons of water. To the slurry is added gradually over a period of 20 minutes approximately 150 pounds of 3-(trimethoxysilyl)-propyloctadecyldimethylammonium chloride (75% nonvolatile in methanol; REQUAT 1977 concentrate from Sanitized Inc.). The slurry is stirred for an additional one hour after the addition of the antimicrobial agent. It is then formed into a pulp sheet on a conventional wet-forming machine and dried to remove water and complete the chemical reaction of the silane with the pulp. The sheets are dried on hot cans with surface temperatures of approximately 400° F.

Staining with Bromophenol Blue confirms the presence of a quaternary ammonium salt group. Samples of the pulp are soaked in water overnight and then redried. A negative test in the extract for quaternary ammonium salt using the Bromophenol Blue test is observed, indicating that the quaternary compound has chemically coupled with the pulp.

Weyerhaeuser Evergreen Summit debonded softwood pulp is combined with the antimicrobially-treated pulp in a ratio of 90 parts by weight to 10 parts by weight and formed into a bonded pulp nonwoven fabric using the airlaid process. The latex binder (HA8 acrylic binder from Rohm & Haas) is applied by spray technique at a level of 20% by weight.

Example 2

Two thousand pounds of wood pulp are charged into a hydroformer along with 12,000 gallons of water. To the slurry is added gradually over a period of 20 minutes approximately 150 pounds of 3-(trimethoxysilyl)-propyloctadecyldimethylammonium chloride (75% nónvolatile in methanol; REQUAT 1977 concentrate from Sanitized Inc.). The slurry is stirred for an additional one hour after the addition of the antimicrobial agent. It is then formed into a pulp sheet on a conventional wet-forming machine and dried to remove water and complete the chemical reaction of the silane with the pulp. The sheets are dried on hot cans with surface temperatures of approximately 400° F.

Staining with Bromophenol Blue confirms the presence of a quaternary ammonium salt group. Samples of the pulp are soaked in water overnight and then redried. A negative test in the extract for quaternary ammonium salt using the Bromophenol Blue test is observed, indicating that the quaternary compound has chemically coupled with the pulp.

Weyerhaeuser Evergreen Summit debonded softwood pulp is combined with the antimicrobially-treated pulp in a ratio of 80 parts by weight to 20 parts by weight and formed into a bonded pulp nonwoven fabric using the airlaid process. The latex binder (HA8 acrylic binder from Rohm & Haas) is applied by spray technique at a level of 20% by weight.

Comparative Example

In a third example, for comparative purposes, 100% Evergreen pulp is formed into an airlaid nonwoven using the same acrylic binder (Rohm & Haas HA8) to which has been added sufficient antimicrobial (REQUAT 1977) so that the finished product contains approximately 1.5% antimicrobial by weight.

Water Absorbency

Water absorbency is measured as follows: Drops of water are carefully placed on the surface of the three fabrics, and a time for penetration is measured. For the products of the first two examples, the penetration time is measured at less than two seconds, whereas with the third fabric the drops tends to remain on the surface for at least two minutes. Thus the fabrics from Examples 1 and 2 show excellent water absorbency typical of nonwovens made by airlaid technology. In contrast, the fabric produced in Example 3 is hydrophobic and water beads up on its surface.

Antimicrobial Activity

The antimicrobial activity of these three fabrics is tested by standard fabric challenge methods. Kill rates are measured for *Escherichia coliformia, Staphylococcus aureus, Aspergillus niger, Candida albacans,* and *Pseudomonus auriginosa.* In all cases, kill rates of approximately 90% are achieved within the first eight hours. After 48 hours, all fabrics provided at least a 3-log kill against these selected organisms. It is concluded, therefore, that the antimicrobial activity of the three materials is essentially the same.

Other embodiments of the invention will be apparent to one skilled in the art from a consideration of the specification or with the practice of the invention disclosed herein. It is intended that the specification and Examples be considered as illustrative only, with the spirit and scope of the invention being indicated by the appended claims.

What is claimed is:

1. An antimicrobially-active nonwoven fabric suitable for use as a wet wiper that comprises fibers and an antimicrobial agent distributed on from 10% through 50% of said fibers, said antimicrobial agent being substantive to said fibers such that said antimicrobial agent is substantially prevented from diffusing from said fabric.

2. An antimicrobially-active nonwoven fabric according to claim 1 comprising: (a) bonded fibers; (b) a binder distributed on said fibers, said binder being present in an amount sufficient to bind said fibers into a fabric; and (c) an antimicrobial agent distributed on from 10% through 50% of said fibers, said antimicrobial agent being substantive to said fibers such that said antimicrobial agent is substantially prevented from diffusing from said fabric.

3. The web of claim 1, wherein said fibers are selected from the group consisting of cellulosic fibers, synthetic fibers, and combinations thereof.

4. The web of claim 2, wherein said fibers are derived from wood pulp.

5. The web of claim 4, wherein said web is airlaid.

6. The web of claim 5, wherein said binder is a latex binder.

7. The web of claim 6, wherein the amount of said binder is in the range of about 5% to about 30% of the total web weight.

8. The web of claim 1, wherein said antimicrobial agent is safe for contact with human skin and eyes.

9. The web of claim 8, wherein said antimicrobial agent is an organosilicon quaternary ammonium salt.

10. The web of claim 2, wherein said antimicrobial agent is an organosilicon quaternary ammonium salt.

11. The web of claim 10, wherein said organosilicon quaternary ammonium salt is selected from the group consisting of those having the formula $$[(RO)_3Si(CH_2)_nNR_1R_2R_3]^+X^-$$

in which R is lower alkyl, n is an integer from 2 through 8, $R_1$ is an alkyl group of 9 through 22 carbon atoms, $R_2$ and $R_3$ are lower alkyl, and X is a pharmaceutically acceptable anion.

12. The web of claim 11, wherein said anion is chloride.

13. The web of claim 12, wherein said salt is 3-(trimethoxysilyl)propyloctadecyldimethylammonium chloride.

14. The web of claim 10, wherein said antimicrobial agent is distributed on from 20% through 40% of fibers in the web.

15. The web of claim 14, wherein the amount of said antimicrobial agent is in the range of 0.1% to about 3% of the total web weight.

16. An airlaid web according to claim 2 comprising cellulosic fibers, a latex binder, and 3-(trimethoxysilyl)propyloctadecyldimethylammonium chloride.

17. A wet wiper comprising a nonwoven fabric according to claim 1.

18. A wet wiper comprising a nonwoven fabric according to claim 2.

* * * * *